(12) United States Patent
Kettlewell et al.

(10) Patent No.: US 9,440,001 B2
(45) Date of Patent: Sep. 13, 2016

(54) ABSORBENT MATERIALS

(71) Applicant: Speciality Fibres and Materials Limited, London (GB)

(72) Inventors: Graeme Kettlewell, London (GB); Phillip Martin Baker, London (GB)

(73) Assignee: Specialty Fibres and Materials Limited, London (GB)

( * ) Notice: Subject to any disclaimer, the term of this patent is extended or adjusted under 35 U.S.C. 154(b) by 0 days.

(21) Appl. No.: 14/199,536

(22) Filed: Mar. 6, 2014

(65) Prior Publication Data

US 2014/0257221 A1    Sep. 11, 2014

(30) Foreign Application Priority Data

Mar. 6, 2013 (GB) .................................. 1303971.4

(51) Int. Cl.
| | |
|---|---|
| *A61F 13/15* | (2006.01) |
| *A61L 26/00* | (2006.01) |
| *A61L 15/60* | (2006.01) |
| *A61F 13/53* | (2006.01) |
| *A61L 15/24* | (2006.01) |
| *A61L 15/28* | (2006.01) |

(52) U.S. Cl.
CPC ............ *A61L 26/0052* (2013.01); *A61F 13/53* (2013.01); *A61L 15/24* (2013.01); *A61L 15/28* (2013.01); *A61L 15/60* (2013.01); *A61L 26/0014* (2013.01); *A61L 26/0023* (2013.01); *A61L 26/0061* (2013.01); *A61F 2013/530306* (2013.01); *A61F 2013/530489* (2013.01); *A61F 2013/530613* (2013.01); *A61F 2013/530708* (2013.01)

(58) Field of Classification Search
CPC .......... A61F 13/53; A61F 13/530306; A61F 13/530489; A61F 13/530613; A61F 13/530708
USPC ......................... 604/358, 367, 368, 370, 372
See application file for complete search history.

(56) References Cited

U.S. PATENT DOCUMENTS

| | | | |
|---|---|---|---|
| 4,142,913 A | 3/1979 | McCorsley, III et al. | |
| 4,144,080 A | 3/1979 | McCorsley, III | |
| 4,145,532 A | 3/1979 | Franks et al. | |
| 4,196,282 A | 4/1980 | Franks et al. | |
| 4,211,574 A | 7/1980 | McCorsley, III et al. | |
| 4,246,221 A | 1/1981 | McCorsley, III | |
| 4,416,698 A | 11/1983 | McCorsley, III | |
| 4,426,228 A | 1/1984 | Brandner et al. | |
| 4,865,596 A | 9/1989 | Weisman et al. | |
| 5,252,284 A | 10/1993 | Jurkovic et al. | |
| 5,311,389 A * | 5/1994 | Howey ......................... | 360/133 |
| 5,366,832 A * | 11/1994 | Hayashi et al. ............. | 429/249 |
| 5,417,909 A | 5/1995 | Michels et al. | |
| 5,599,585 A | 2/1997 | Cohen | |
| 5,656,355 A | 8/1997 | Cohen | |
| 5,814,094 A | 9/1998 | Flick et al. | |
| 5,848,995 A | 12/1998 | Walder | |
| 5,985,301 A | 11/1999 | Nakamura et al. | |
| 6,087,549 A | 7/2000 | Flick et al. | |
| 6,113,636 A | 9/2000 | Ogle | |
| 6,190,407 B1 | 2/2001 | Ogle | |
| 6,191,335 B1 * | 2/2001 | Robinson ..................... | 602/41 |
| 6,194,332 B1 | 2/2001 | Rock et al. | |
| 6,218,910 B1 | 4/2001 | Miller | |
| 6,224,898 B1 | 5/2001 | Balogh et al. | |
| 6,267,782 B1 | 7/2001 | Ogle | |
| 6,281,515 B1 | 8/2001 | Demeo et al. | |
| 6,459,091 B1 | 10/2002 | Demeo et al. | |
| 6,501,343 B2 | 12/2002 | Miller | |
| 6,576,338 B1 | 6/2003 | Meijer et al. | |
| 6,582,411 B1 * | 6/2003 | Carstens ........... | A61F 13/15723 604/358 |
| 6,592,888 B1 | 7/2003 | Jensen et al. | |
| 6,599,523 B2 | 7/2003 | Cohen | |
| 6,602,811 B1 | 8/2003 | Rock et al. | |
| 6,627,785 B1 | 9/2003 | Cohen | |
| 6,630,016 B2 | 10/2003 | Koslow | |
| 6,660,172 B2 | 12/2003 | Koslow | |
| 6,686,754 B2 | 2/2004 | Miller | |
| 6,692,773 B2 | 2/2004 | Burrell et al. | |
| 6,716,895 B1 | 4/2004 | Terry | |
| 6,719,987 B2 | 4/2004 | Langford et al. | |
| 6,720,006 B2 | 4/2004 | Hanke et al. | |
| 6,723,350 B2 | 4/2004 | Bowlby et al. | |
| 6,723,428 B1 | 4/2004 | Foss et al. | |
| 6,822,034 B2 | 11/2004 | Bast et al. | |
| 6,828,578 B2 | 12/2004 | Demeo et al. | |
| 6,835,311 B2 | 12/2004 | Koslow | |
| 6,841,244 B2 | 1/2005 | Foss et al. | |
| 6,841,791 B2 | 1/2005 | Demeo et al. | |
| 6,861,570 B1 | 3/2005 | Flick et al. | |

(Continued)

FOREIGN PATENT DOCUMENTS

| | | |
|---|---|---|
| DE | 19722932 | 12/1998 |
| DE | 10309558 | 9/2004 |

(Continued)

OTHER PUBLICATIONS ohioline.osu.edu, ohio state, p. 1.*

(Continued)

*Primary Examiner* — Bradley Philips

(74) *Attorney, Agent, or Firm* — Wells St. John P.S.

(57) ABSTRACT

An absorbent material for use in wound dressings is provided. The absorbent material comprises a blend of a superabsorbent gel-forming fiber and a non gel-forming fiber, wherein the blend of fiber does not comprise a superabsorbent gel-forming fiber formed from a polysaccharide.

6 Claims, No Drawings

(56) References Cited

U.S. PATENT DOCUMENTS

| | | |
|---|---|---|
| 6,866,704 B2 | 3/2005 | Koslow |
| 6,872,311 B2 | 3/2005 | Koslow |
| 6,905,711 B1 | 6/2005 | Tullo et al. |
| 6,911,437 B2 | 6/2005 | Cohen |
| 6,913,154 B2 | 7/2005 | Koslow |
| 6,917,210 B2 | 7/2005 | Miller |
| 6,939,568 B2 | 9/2005 | Burrell et al. |
| 6,946,196 B2 | 9/2005 | Foss et al. |
| 6,949,598 B2 | 9/2005 | Terry |
| 6,953,604 B2 | 10/2005 | Koslow |
| 6,959,820 B2 | 11/2005 | Koslow |
| 6,979,491 B2 | 12/2005 | Yan et al. |
| 6,989,156 B2 | 1/2006 | Gillis |
| 6,989,157 B2 | 1/2006 | Gillis et al. |
| 6,998,058 B2 | 2/2006 | Koslow |
| 7,001,617 B2 | 2/2006 | Burrell et al. |
| 7,005,556 B1 | 2/2006 | Flick et al. |
| 7,008,537 B2 | 3/2006 | Koslow |
| 7,008,647 B2 | 3/2006 | Burrell et al. |
| 7,011,753 B2 | 3/2006 | Koslow |
| 7,019,391 B2 | 3/2006 | Tran |
| 7,078,060 B2 | 7/2006 | Burrell et al. |
| 7,087,249 B2 | 8/2006 | Burrell et al. |
| 7,118,761 B2 | 10/2006 | Canada et al. |
| 7,141,518 B2 | 11/2006 | MacDonald et al. |
| 7,144,533 B2 | 12/2006 | Koslow |
| 7,179,849 B2 | 2/2007 | Terry |
| 7,201,925 B2 | 4/2007 | Gillis |
| 7,214,847 B1 | 5/2007 | Flick et al. |
| 7,229,689 B2 | 6/2007 | Qin et al. |
| 7,230,153 B2 | 6/2007 | Flick et al. |
| 7,241,388 B2 | 7/2007 | Koslow |
| 7,255,881 B2 | 8/2007 | Gillis et al. |
| 7,276,166 B2 | 10/2007 | Koslow |
| 7,287,650 B2 | 10/2007 | Koslow |
| 7,291,762 B2 | 11/2007 | Flick et al. |
| 7,296,691 B2 | 11/2007 | Koslow |
| 7,300,673 B2 | 11/2007 | Djokic |
| 7,330,369 B2 | 2/2008 | Tran |
| 7,375,417 B2 | 5/2008 | Tran |
| 7,378,156 B2 | 5/2008 | Terry |
| 7,410,650 B2 | 8/2008 | Lin |
| 7,427,416 B2 | 9/2008 | Gillis et al. |
| 7,455,854 B2 | 11/2008 | Gower et al. |
| 7,462,753 B2 | 12/2008 | Yu et al. |
| 7,470,437 B2 | 12/2008 | Burrell et al. |
| 7,476,889 B2 | 1/2009 | Demeo et al. |
| 7,489,537 B2 | 2/2009 | Tran |
| 7,514,248 B2 | 4/2009 | Gower et al. |
| 7,514,249 B2 | 4/2009 | Gower et al. |
| 7,544,496 B2 | 6/2009 | Gower et al. |
| 7,547,449 B2 | 6/2009 | Gower et al. |
| 7,630,227 B2 | 12/2009 | Tran |
| 7,655,112 B2 | 2/2010 | Koslow |
| 7,671,398 B2 | 3/2010 | Tran |
| 7,687,076 B2 | 3/2010 | Djokic |
| 7,745,509 B2 | 6/2010 | Burton et al. |
| 7,775,998 B2 | 8/2010 | Riesinger |
| 7,842,306 B2 | 11/2010 | Cowan et al. |
| 7,862,624 B2 | 1/2011 | Tran |
| 7,864,560 B2 | 1/2011 | Tran |
| 7,951,853 B2 | 5/2011 | Ismail et al. |
| 7,959,624 B2 | 6/2011 | Riesinger |
| 7,989,674 B2 | 8/2011 | Flick et al. |
| 7,998,504 B2 | 8/2011 | Djokic |
| 8,021,685 B2 | 9/2011 | Cowan et al. |
| 8,034,454 B2 | 10/2011 | Terry et al. |
| 8,056,733 B2 | 11/2011 | Koslow |
| 8,084,762 B2 | 12/2011 | Tran |
| 8,093,444 B2 | 1/2012 | Flick et al. |
| 8,118,791 B2 | 2/2012 | Flick et al. |
| 8,118,792 B2 | 2/2012 | Effing et al. |
| 8,118,793 B2 | 2/2012 | Effing et al. |
| 8,123,730 B2 | 2/2012 | Effing et al. |
| 8,124,826 B2 | 2/2012 | Greenhalgh et al. |
| 8,183,167 B1 | 5/2012 | Delattre et al. |
| 8,187,626 B2 | 5/2012 | Cohen |
| 8,193,267 B2 | 6/2012 | Burton et al. |
| 8,217,220 B2 | 7/2012 | Abbas et al. |
| 8,283,513 B2 | 10/2012 | Flick et al. |
| 8,293,964 B2 | 10/2012 | Flick et al. |
| 8,334,524 B2 | 12/2012 | Demeo et al. |
| 8,343,535 B2 | 1/2013 | Burd et al. |
| 8,361,553 B2 | 1/2013 | Karandikar |
| 8,367,089 B2 | 2/2013 | Wan et al. |
| 8,394,403 B2 | 3/2013 | Cowan et al. |
| 8,449,514 B2 | 5/2013 | Flick et al. |
| 8,450,716 B2 | 5/2013 | Tran |
| 8,455,710 B2 | 6/2013 | Flick et al. |
| 8,461,410 B2 | 6/2013 | Addison et al. |
| 8,613,363 B2 | 12/2013 | Koslow |
| 2001/0035800 A1 | 11/2001 | Miller |
| 2001/0055622 A1 | 12/2001 | Langford et al. |
| 2002/0012693 A1 | 1/2002 | Cohen |
| 2002/0043631 A1 | 4/2002 | Demeo et al. |
| 2002/0051824 A1 | 5/2002 | Burrell et al. |
| 2002/0064551 A1 | 5/2002 | Cohen |
| 2002/0082340 A1 | 6/2002 | Bast et al. |
| 2002/0099449 A1 | 7/2002 | Speitling et al. |
| 2002/0122832 A1 | 9/2002 | Hanke et al. |
| 2002/0172709 A1 | 11/2002 | Nielsen et al. |
| 2002/0182265 A1 | 12/2002 | Bowlby et al. |
| 2002/0192298 A1 | 12/2002 | Burrell et al. |
| 2003/0010939 A1 | 1/2003 | Demeo et al. |
| 2003/0021854 A1 | 1/2003 | Burrell et al. |
| 2003/0049300 A1 | 3/2003 | Terry |
| 2003/0054046 A1 | 3/2003 | Burrell et al. |
| 2003/0067316 A1 | 4/2003 | Miller |
| 2003/0072810 A1 | 4/2003 | Burrell |
| 2003/0086977 A1 | 5/2003 | Gillis |
| 2003/0099718 A1 | 5/2003 | Burrell et al. |
| 2003/0130638 A1* | 7/2003 | Baker ............... A61F 13/15626 604/368 |
| 2003/0140785 A1 | 7/2003 | Koslow |
| 2003/0141261 A1 | 7/2003 | Koslow |
| 2003/0153889 A1* | 8/2003 | Gibbs ........................ 604/385.3 |
| 2003/0168401 A1 | 9/2003 | Koslow |
| 2003/0170314 A1 | 9/2003 | Burrell et al. |
| 2003/0170453 A1 | 9/2003 | Foss et al. |
| 2003/0177909 A1 | 9/2003 | Koslow |
| 2003/0180346 A1 | 9/2003 | Woods |
| 2003/0180378 A1 | 9/2003 | Gillis et al. |
| 2003/0180379 A1 | 9/2003 | Burrell et al. |
| 2003/0185889 A1 | 10/2003 | Cheng et al. |
| 2003/0185901 A1 | 10/2003 | Burrell et al. |
| 2003/0190851 A1 | 10/2003 | Yan et al. |
| 2003/0194444 A1 | 10/2003 | Burrell et al. |
| 2003/0196963 A1 | 10/2003 | Koslow |
| 2003/0196964 A1 | 10/2003 | Koslow |
| 2003/0200868 A1 | 10/2003 | Koslow |
| 2003/0201231 A1 | 10/2003 | Koslow |
| 2003/0203046 A1 | 10/2003 | Burrell et al. |
| 2003/0205529 A1 | 11/2003 | Koslow |
| 2003/0205530 A1 | 11/2003 | Koslow |
| 2003/0205531 A1 | 11/2003 | Koslow |
| 2003/0206944 A1 | 11/2003 | Cohen |
| 2003/0206966 A1 | 11/2003 | Burrell et al. |
| 2003/0213750 A1 | 11/2003 | Koslow |
| 2003/0232071 A1 | 12/2003 | Gower et al. |
| 2004/0001880 A1 | 1/2004 | Bowler et al. |
| 2004/0004196 A1 | 1/2004 | Demeo et al. |
| 2004/0030276 A1 | 2/2004 | Flick et al. |
| 2004/0031749 A1 | 2/2004 | Koslow |
| 2004/0038609 A1 | 2/2004 | Mayer |
| 2004/0049145 A1 | 3/2004 | Flick et al. |
| 2004/0084378 A1 | 5/2004 | Koslow |
| 2004/0116551 A1 | 6/2004 | Terry |
| 2004/0129112 A1 | 7/2004 | Gillis |
| 2004/0131562 A1 | 7/2004 | Gower et al. |
| 2004/0131698 A1 | 7/2004 | Gillis et al. |
| 2004/0140822 A1 | 7/2004 | Miller |
| 2004/0157073 A1 | 8/2004 | Bowlby et al. |
| 2004/0176312 A1 | 9/2004 | Gillis |
| 2004/0178142 A1 | 9/2004 | Koslow |

(56) References Cited

U.S. PATENT DOCUMENTS

| | | |
|---|---|---|
| 2004/0191329 A1 | 9/2004 | Burrell et al. |
| 2004/0191500 A1 | 9/2004 | Foss et al. |
| 2004/0197553 A1 | 10/2004 | Foss et al. |
| 2004/0202860 A1 | 10/2004 | Foss et al. |
| 2004/0209059 A1 | 10/2004 | Foss et al. |
| 2004/0214495 A1 | 10/2004 | Foss et al. |
| 2004/0229034 A1 | 11/2004 | Djokic |
| 2004/0234604 A1 | 11/2004 | Mecking et al. |
| 2004/0241213 A1 | 12/2004 | Bray |
| 2005/0003728 A1 | 1/2005 | Foss et al. |
| 2005/0008861 A1 | 1/2005 | Yadav et al. |
| 2005/0011827 A1 | 1/2005 | Koslow |
| 2005/0019568 A1 | 1/2005 | Foss et al. |
| 2005/0035327 A1 | 2/2005 | Canada et al. |
| 2005/0037057 A1 | 2/2005 | Schuette et al. |
| 2005/0037058 A1 | 2/2005 | Cowan et al. |
| 2005/0037680 A1 | 2/2005 | Canada et al. |
| 2005/0051487 A1 | 3/2005 | Koslow |
| 2005/0058835 A1 | 3/2005 | Bayston et al. |
| 2005/0064020 A1 | 3/2005 | Schuette et al. |
| 2005/0085144 A1 | 4/2005 | Fish et al. |
| 2005/0101213 A1 | 5/2005 | Foss et al. |
| 2005/0101900 A1 | 5/2005 | Qin et al. |
| 2005/0106390 A1 | 5/2005 | Foss et al. |
| 2005/0124724 A1 | 6/2005 | Burton et al. |
| 2005/0129624 A1 | 6/2005 | Burrell et al. |
| 2005/0136100 A1 | 6/2005 | Foss et al. |
| 2005/0136128 A1 | 6/2005 | Gillis et al. |
| 2005/0147657 A1 | 7/2005 | Canada et al. |
| 2005/0152990 A1 | 7/2005 | Gower et al. |
| 2005/0191355 A1 | 9/2005 | Foss et al. |
| 2005/0211930 A1 | 9/2005 | Demeo et al. |
| 2005/0218397 A1 | 10/2005 | Tran |
| 2005/0218398 A1 | 10/2005 | Tran |
| 2005/0228351 A1 | 10/2005 | Bourgeois et al. |
| 2005/0229328 A1 | 10/2005 | Tran |
| 2005/0230822 A1 | 10/2005 | Tran |
| 2005/0231855 A1 | 10/2005 | Tran |
| 2005/0244484 A1 | 11/2005 | Flick et al. |
| 2005/0271743 A1 | 12/2005 | Burrell et al. |
| 2006/0057191 A1 | 3/2006 | Wellinghoff |
| 2006/0083777 A1 | 4/2006 | Burrell et al. |
| 2006/0083792 A1 | 4/2006 | Gillis et al. |
| 2006/0115541 A1 | 6/2006 | Gillis et al. |
| 2006/0127462 A1 | 6/2006 | Cowan et al. |
| 2006/0141015 A1 | 6/2006 | Tessier et al. |
| 2006/0145326 A1 | 7/2006 | Tran |
| 2006/0149182 A1 | 7/2006 | Addison et al. |
| 2006/0159732 A1 | 7/2006 | Greenhalgh et al. |
| 2006/0160448 A1 | 7/2006 | Abraham et al. |
| 2006/0198209 A1 | 9/2006 | Tran |
| 2006/0202382 A1 | 9/2006 | Lin |
| 2006/0204580 A1 | 9/2006 | Cheng et al. |
| 2006/0204581 A1 | 9/2006 | Cheng et al. |
| 2006/0204591 A1 | 9/2006 | Burrell et al. |
| 2006/0240067 A1 | 10/2006 | Chartier et al. |
| 2006/0260674 A1 | 11/2006 | Tran |
| 2006/0264796 A1 | 11/2006 | Flick et al. |
| 2006/0283567 A1 | 12/2006 | Bauer et al. |
| 2007/0003603 A1 | 1/2007 | Cornell et al. |
| 2007/0009586 A1 | 1/2007 | Cohen |
| 2007/0051366 A1 | 3/2007 | Hannsman et al. |
| 2007/0060691 A1 | 3/2007 | Kim |
| 2007/0087023 A1 | 4/2007 | Ismail et al. |
| 2007/0098806 A1 | 5/2007 | Ismail et al. |
| 2007/0100269 A1 | 5/2007 | Greenhalgh et al. |
| 2007/0122462 A1 | 5/2007 | Chandra et al. |
| 2007/0134307 A1 | 6/2007 | Robb et al. |
| 2007/0148449 A1 | 6/2007 | Winterhalter |
| 2007/0179522 A1 | 8/2007 | Flick et al. |
| 2007/0207335 A1 | 9/2007 | Karandikar et al. |
| 2007/0218298 A1 | 9/2007 | Terry |
| 2007/0243380 A1 | 10/2007 | Hayhurst et al. |
| 2007/0259196 A1 | 11/2007 | Ruhle et al. |
| 2007/0275043 A1 | 11/2007 | Bradford et al. |
| 2007/0286895 A1 | 12/2007 | Bowler et al. |
| 2007/0293799 A1 | 12/2007 | Yu et al. |
| 2007/0298064 A1 | 12/2007 | Koslow |
| 2008/0004559 A1 | 1/2008 | Riesinger |
| 2008/0009812 A1 | 1/2008 | Riesinger |
| 2008/0014286 A1 | 1/2008 | Gillis et al. |
| 2008/0033506 A1 | 2/2008 | Flick et al. |
| 2008/0053922 A1 | 3/2008 | Bumin et al. |
| 2008/0064997 A1 | 3/2008 | Flick et al. |
| 2008/0075650 A1 | 3/2008 | Djokic |
| 2008/0075860 A1 | 3/2008 | Djokic |
| 2008/0096449 A1 | 4/2008 | Bourgeois et al. |
| 2008/0102122 A1 | 5/2008 | Khanolkar et al. |
| 2008/0114279 A1 | 5/2008 | Flick et al. |
| 2008/0119773 A1 | 5/2008 | Flick et al. |
| 2008/0125687 A1 | 5/2008 | Flick et al. |
| 2008/0199536 A1 | 8/2008 | Terry |
| 2008/0199623 A1 | 8/2008 | Terry |
| 2008/0213394 A1 | 9/2008 | Ismail et al. |
| 2008/0233161 A1 | 9/2008 | Djokic |
| 2008/0239791 A1 | 10/2008 | Tran |
| 2008/0241229 A1 | 10/2008 | Li et al. |
| 2008/0241795 A1 | 10/2008 | Block et al. |
| 2008/0249453 A1 | 10/2008 | Effing et al. |
| 2008/0249485 A1 | 10/2008 | Effing et al. |
| 2008/0249486 A1 | 10/2008 | Effing et al. |
| 2008/0286346 A1 | 11/2008 | Effing et al. |
| 2008/0299160 A1 | 12/2008 | Agboh et al. |
| 2009/0000007 A1 | 1/2009 | Demeo et al. |
| 2009/0004474 A1 | 1/2009 | Luo |
| 2009/0035342 A1 | 2/2009 | Cornell et al. |
| 2009/0081312 A1 | 3/2009 | Block et al. |
| 2009/0114857 A1 | 5/2009 | Demeo et al. |
| 2009/0116277 A1 | 5/2009 | Tran |
| 2009/0130160 A1 | 5/2009 | Dugan |
| 2009/0214771 A1 | 8/2009 | Kang et al. |
| 2009/0220560 A1 | 9/2009 | Wan et al. |
| 2009/0247973 A1 | 10/2009 | Yeh et al. |
| 2009/0252861 A1 | 10/2009 | Tessier et al. |
| 2009/0259157 A1 | 10/2009 | Thomas |
| 2009/0263468 A1 | 10/2009 | Abbott et al. |
| 2009/0275906 A1 | 11/2009 | Abbas et al. |
| 2009/0293882 A1 | 12/2009 | Terry |
| 2010/0003296 A1 | 1/2010 | Cheng et al. |
| 2010/0015208 A1 | 1/2010 | Kershaw et al. |
| 2010/0021552 A1 | 1/2010 | Hayes et al. |
| 2010/0042034 A1 | 2/2010 | Riesinger |
| 2010/0044289 A1 | 2/2010 | Koslow |
| 2010/0055157 A1 | 3/2010 | Gunn |
| 2010/0073995 A1 | 3/2010 | Tran |
| 2010/0098949 A1 | 4/2010 | Burton et al. |
| 2010/0113871 A1 | 5/2010 | Franken et al. |
| 2010/0124861 A1 | 5/2010 | Wendler |
| 2010/0155692 A1 | 6/2010 | Tran |
| 2010/0196448 A1 | 8/2010 | Burd et al. |
| 2010/0221311 A1 | 9/2010 | Cohen |
| 2010/0221312 A1 | 9/2010 | Cohen |
| 2010/0233245 A1 | 9/2010 | Narayana |
| 2010/0233273 A1 | 9/2010 | Burton et al. |
| 2010/0262096 A1 | 10/2010 | Hall |
| 2010/0291174 A1 | 11/2010 | Barcikowski et al. |
| 2010/0291184 A1 | 11/2010 | Clark et al. |
| 2011/0034894 A1 | 2/2011 | Riesinger |
| 2011/0040289 A1 | 2/2011 | Cowan et al. |
| 2011/0052698 A1 | 3/2011 | Benoit et al. |
| 2011/0091557 A1 | 4/2011 | Buckley et al. |
| 2011/0110141 A1 | 5/2011 | Tran |
| 2011/0110999 A1 | 5/2011 | Bogana et al. |
| 2011/0115512 A1 | 5/2011 | Miller |
| 2011/0123597 A1 | 5/2011 | Cohen |
| 2011/0135846 A1 | 6/2011 | Seino et al. |
| 2011/0142898 A1 | 6/2011 | Fan |
| 2011/0152843 A1 | 6/2011 | Lundahl et al. |
| 2011/0171321 A1 | 7/2011 | Luchsinger et al. |
| 2011/0189287 A1 | 8/2011 | Abbott et al. |
| 2011/0232653 A1 | 9/2011 | Imashiro et al. |
| 2011/0262556 A1 | 10/2011 | Brooks et al. |
| 2011/0272619 A1 | 11/2011 | Wang et al. |
| 2011/0275513 A1* | 11/2011 | Tian et al. ............ 502/402 |

(56) References Cited

U.S. PATENT DOCUMENTS

| | | |
|---|---|---|
| 2011/0280928 A1 | 11/2011 | Cowan et al. |
| 2011/0306699 A1 | 12/2011 | Whang et al. |
| 2011/0313373 A1 | 12/2011 | Riesinger |
| 2012/0034432 A1 | 2/2012 | Cotton |
| 2012/0064138 A1 | 3/2012 | Beveridge et al. |
| 2012/0091429 A1 | 4/2012 | Tran |
| 2012/0094120 A1 | 4/2012 | Foss et al. |
| 2012/0107592 A1 | 5/2012 | Griesser et al. |
| 2012/0143157 A1 | 6/2012 | Riesinger |
| 2012/0164449 A1 | 6/2012 | Foss |
| 2012/0183674 A1 | 7/2012 | Bonn-Savage et al. |
| 2012/0202043 A1 | 8/2012 | Bonn-Savage et al. |
| 2012/0222826 A1 | 9/2012 | Foss |
| 2012/0276205 A1 | 11/2012 | Weissman et al. |
| 2012/0282321 A1 | 11/2012 | Cohen |
| 2012/0299175 A1 | 11/2012 | Tran |
| 2013/0052256 A1 | 2/2013 | Smith |
| 2013/0066288 A1 | 3/2013 | Lin |
| 2013/0122321 A1 | 5/2013 | Karandikar et al. |
| 2013/0152309 A1 | 6/2013 | Bray |
| 2013/0163310 A1 | 6/2013 | Tran |
| 2013/0197460 A1 | 8/2013 | Shaw et al. |
| 2013/0211308 A1 | 8/2013 | Wan et al. |
| 2013/0216598 A1 | 8/2013 | Wang et al. |
| 2013/0217649 A1 | 8/2013 | Woods |
| 2013/0231640 A1 | 9/2013 | Chen et al. |

FOREIGN PATENT DOCUMENTS

| | | |
|---|---|---|
| DE | 202005010978 | 10/2005 |
| DE | 102005031711 | 6/2007 |
| DE | 202008004240 | 7/2008 |
| DE | 102007025714 | 12/2008 |
| DE | 10 2007 049430 | 4/2009 |
| DE | 10 2007 063294 | 7/2009 |
| DE | 102009036302 | 2/2011 |
| DE | 202010014723 | 11/2011 |
| EP | 0306262 | 3/1989 |
| EP | 1656914 | 5/2006 |
| EP | 1666077 | 6/2006 |
| EP | 1947167 | 7/2008 |
| EP | 2140958 | 1/2010 |
| EP | 2498829 | 9/2012 |
| GB | 2401879 | 11/2004 |
| GB | 0905341.4 | 3/2009 |
| GB | 2476133 | 6/2011 |
| GB | 1303971.4 | 8/2013 |
| WO | WO 98/31402 | 7/1998 |
| WO | WO 01/06047 | 1/2001 |
| WO | WO 01/38615 | 5/2001 |
| WO | WO 01/41819 | 6/2001 |
| WO | WO 03/046273 | 6/2003 |
| WO | WO 2005/018769 | 3/2005 |
| WO | WO 2006/021155 | 3/2006 |
| WO | WO 2007/029597 | 3/2007 |
| WO | WO 2007/046806 | 4/2007 |
| WO | WO 2007/078203 | 7/2007 |
| WO | WO 2008/010199 | 1/2008 |
| WO | WO 2008/024426 | 2/2008 |
| WO | WO 2008/098420 | 8/2008 |
| WO | WO 2008/100163 | 8/2008 |
| WO | WO 2008/101417 | 8/2008 |
| WO | WO 2009/141278 | 11/2009 |
| WO | WO 2010/123392 | 10/2010 |
| WO | WO 2011/073697 | 6/2011 |
| WO | WO 2011/076203 | 6/2011 |
| WO | WO 2011/101857 | 8/2011 |
| WO | WO 2012/075658 | 6/2012 |
| WO | WO 2012/106983 | 8/2012 |
| WO | WO 2012/127326 | 9/2012 |
| WO | WO 2013/123507 | 8/2013 |
| WO | WO 2013/123509 | 8/2013 |

OTHER PUBLICATIONS http://www.m2polymer.com/html/super_absorbent_fibers.html; Oct. 17, 2008 (see provided copy).*
http://www.m2polymer.com/pdf/Tech%20Sheet_Oasis%20SAF%206mm_M2PT.pdf; Nov. 11, 2015.*

* cited by examiner

ABSORBENT MATERIALS

CROSS REFERENCE TO RELATED APPLICATION

This application claims priority to GB Patent Application No. 1303971.4, which was filed on 6 Mar. 2013, the teachings of which are incorporated herein by reference.

The present invention relates to superabsorbent materials useful in the manufacture of absorbent articles such as wound dressings, and in particular wound dressings for the treatment of chronic, non-healing wounds.

Absorbent fibres useful as components in advanced wound care dressings are known in the art, particularly fibres based on alginic acid, carboxymethylcellulose (CMC), carboxymethylchitosan, cellulose ethyl sulfonate (CES) and salts thereof. Fibrous wound dressings may typically absorb up to 20-25 g of wound exudate per 100 $cm^2$ dressing. Heavily exuding wounds such as diabetic leg ulcers may exude 5-10 g of liquid per 10 $cm^2$ per 24 h. A wound of say 80 $cm^2$ would therefore overwhelm a 100 $cm^2$ fibrous wound dressing within a few hours, necessitating change of the dressing. To partly overcome this, superabsorbent materials are often used in advanced wound care dressings.

Standard superabsorbent materials, such as those based upon polyacrylic acid and its salts, soften and lose their mechanical strength when they absorb fluid and become wet. This is particularly undesirable when the material is intended for use as wound dressing where it may be necessary to remove a used dressing in one piece before it is replaced. A loss of mechanical strength may lead to break up of the dressing which may lead to complications, pain and discomfort for the patient and an extension of treatment time.

Powdered superabsorbent materials are used, often in combination with a bulking agent such as cellulose fluff, in absorbent wound dressings such as Sorbion Sachet S (Sorbion Gmbh & Co, Germany) and Vliwasorb, (Lohmann and Rauscher Gmbh & Co, Austria). In these dressings the poor mechanical strength of the superabsorbent powder when wet is overcome by enclosing the material in a non-woven outer pouch. The pouch may be made of a textile material of a soft texture, for example a perforated or mesh-type hydrophobic fleece-type film such as polyethylene or polypropylene film or a natural-fibre fabric or fleece. Dressings such as the Sorbion Sachet S and Vliwasorb dressings are also not suitable for use in cavity wounds. Due to the very large absorbent capacity of these dressings, on absorbing wound exudate they swell to many times their original dimension, potentially causing pain and trauma to the patient and extending treatment times. Dressings containing a superabsorbent material in the form of a powder may also disadvantageously exhibit gel blocking where the surface of a superabsorbent particle gels, preventing fluid transfer and leaving the inside of the particle dry. This may reduce the overall absorbency of the dressing and may potentially lead to harmful maceration of the periwound skin. Due to the very large absorbent capacity of these dressings they lack flexibility when wet.

Other wound dressings such as Askina Absorb+ (B. Braun Melsungen AG) and Sorbsan Plus SA (Aspen Medical, UK) seek to overcome this by using a superabsorbent fibre instead of a powdered material. Both contain a fabric comprising cellulose fluff pulp, superabsorbent fibre and a thermoplastic bicomponent fibre. The thermoplastic bicomponent fibre is used to fuse together the individual filaments of superabsorbent fibre and fluff pulp which would otherwise be unusably weak when wet. The superabsorbent fibres used in Askina Absorb+ are contained within a non-woven outer pouch that, prima facie, is not dissimilar to the type used in products such as Sorbion Sachet A or Vliwasorb. The superabsorbent fibres used in Sorbsan Plus SA, present in a multilaminar construction of a fabric comprising cellulose fluff pulp, superabsorbent fibre and a thermoplastic bicomponent fibre, are needle bonded to a wound contacting calcium alginate layer. The backing layer may comprise two outer layers which are a blend of fluff pulp and low melt binder, and a core absorbency layer which is a blend of fluff pulp, gel-forming polymer superabsorbent fibres and low melt binder. However, due to their multiple layers these dressings are very thick and inflexible, having a typical weight of 250-300 $g/m^2$. Because of the large amount of non absorbent thermoplastic fibre in the cellulose fluff pulp, superabsorbent fibre and thermoplastic bicomponent fibre containing fabric, the absorbency per gram is relatively low, comparable to or only slightly better than that of conventional fibrous wound dressings.

Cotton in GB0905341.4 seeks to provide a method for reinforcing superabsorbent materials. A layered arrangement is formed with a single inner absorbent layer sandwiched between two outer reinforcing layers. Cotton discloses that the application of high frequency mechanical vibrations to the layered arrangement is able to bring about the generation of localised heat by friction. Because the layered arrangement contains a thermoplastic material that fuses when heated, the heat generated causes the welding of those layers together to form a composite absorbent material. This method of reinforcing an absorbent material relies on ultrasonically welding together at least two different fabrics, at least one of which contains a thermoplastic synthetic fibre. Synthetic thermoplastic fibres are disadvantageous in that they do not absorb fluid and in this application are adding mass and cost to the absorbent article without adding to the capability to absorb fluid.

It is an object of the present invention to mitigate at least some of the problems described above.

According to a first aspect of the present invention, there is provided an absorbent material comprising a blend of a superabsorbent gel-forming fibre and a non gel-forming fibre, wherein the blend of fibres does not comprise a superabsorbent gel-forming fibre formed from a polysaccharide.

According to a second aspect of the present invention, there is provided an absorbent material comprising a blend of fibres, the blend of fibres consisting of a single type of superabsorbent gel-forming fibre and a non gel-forming fibre.

By the term 'blend' it will be appreciated that the superabsorbent gel-forming fibres and the non gel-forming fibres are intimately mixed so as to form a homogenous mixture of fibres.

It will be understood that the statements below apply equally to the first and second aspects of the invention, unless stated otherwise.

The superabsorbent gel-forming fibre may be formed from a superabsorbent polymer. It will be understood that a superabsorbent polymer is a polymer which is capable of absorbing water in an amount as much as 500 times its own weight. In some embodiments, the superabsorbent polymer is capable of absorbing water in an amount of more than 10, more than 20, more than 30, more than 40, more than 60 or more than 100 times its own weight. In some embodiments, the super-absorbent gel-forming fibre is capable of absorbing at least 15, at least 20, at least 30, at least 50, at least 75 or at least 100 g of liquid (e.g. water or saline) per g of fibre. In some embodiments, the super-absorbent polymer is capable of absorbing more than 20, more than 40, more than 60, more than 80 or more than 100 g of liquid (e.g. water or saline) per gram of fibre.

In some embodiments, the superabsorbent polymer is a synthetic polymer. Suitable synthetic polymers may be prepared from polymerizable, unsaturated, acid-containing monomers, such as unsaturated carboxylic acids and acid anhydrides, unsaturated sulfonic acids and combinations thereof. Useful unsaturated carboxylic acid and carboxylic acid anhydride monomers include, e.g., acrylic acid, methacrylic acid, ethacrylic acid, chloroacrylic acid, cyanoacrylic acid, crotonic acid, phenylacrylic acid, acryloxypropionic acid, sorbic acid, chlorosorbic acid, angelic acid, cinnamic acid, p-chlorocinnamic acid, stearylacrylic acid, itaconic acid, citraconic acid, mesaconic acid, glutaconic acid, aconitic acid, maleic acid, fumaric acid, tricarboxyethylene acid anhydride, maleic acid anhydride, and combinations thereof.

Useful unsaturated sulfonic acid monomers for the preparation of synthetic superabsorbent polymers include aliphatic and aromatic vinyl sulfonic acids (e.g., vinylsulfonic acid, allyl sulfonic acid, vinyl toluene sulfonic acid and styrene sulfonic acid), acrylic and methacrylic sulfonic acids (e.g., sulfoethyl acrylate, sulfoethyl methacrylate, sulfopropyl acrylate, sulfopropyl methacrylate, 2-hydroxy-3-methacryloxypropyl sulfonic acid and 2-acrylamide-2-methylpropane sulfonic acid), and combinations thereof.

In some embodiments, the superabsorbent polymer is selected from the group consisting of: polyacrylates or co-polymers thereof; polymers of anhydrides, such as poly (maleic anhydride), or co-polymers thereof; polymers with carboxylic acid groups or salts thereof, such as polymers of acrylic acid, maleic acid, methacrylic acid or derivatives thereof; polymers of acrylamide (e.g. polyacrylamide) or co-polymers thereof; polyethylene oxide (PEO); polyvinyl alcohol (PVOH); graft co-polymers; or mixtures thereof. Suitable polymers of acrylamide or copolymers thereof include polyacrylamide, polyAMPs (poly-acrylamido-2-methylpropane sulfonic acid) or its sodium salt, and acrylamide-co-acrylic acid.

In some embodiments, the superabsorbent polymer is a polyacrylate or copolymer thereof. Polyacrylates are a broad group of synthetic polymers derived from monomers which include esters of acrylic acid, for example poly(hydroxyl methacrylate), and salts of polymers of acrylic acid and derivatives thereof.

Suitable polyacrylates or copolymers thereof for use in the invention include sodium polyacrylate, sodium polymethacrylate, and co-polymers of acrylic acid with other monomers. Further examples include co-polymers of acrylic acid with vinyl pyrrolidone monomers, optionally with a diacrylate cross-linker, co-polymers of acrylic acid with maleic acid or hydrolysed maleic anhydride. Co-polymers may also comprise olefins, such as ethylene.

In some embodiments the polymers or co-polymers are cross-linked.

One example of polyacrylate fibres is 'SAF'™, commercially available fibres sold by Technical Absorbent Limited (Grimsby, UK). SAF™ is formed from a cross-linked polymer of acrylic acid (AA) methylacrylate (MA) and a small quantity of special acrylate/methylacrylate monomer (SAMM) in which the acrylic acid is partially neutralised to the sodium salt of acrylic acid (AANa). SAF™ fibres are available in different staple lengths, linear density and with different degrees of cross linking to give different absorbency levels. Thus, in some embodiments the superabsorbent gel-forming fibre is SAF.

In some embodiments of the second aspect of the invention, the superabsorbent gel-forming fibre is formed from a graft polymer. Graft polymers are polymers grafted onto a backbone of another suitable polymer, such as a polysaccharide backbone. The graft polymer may be a homopolymer or a copolymer. Suitable polymers for the formation of graft polymers include polyacrylic acid or acrylamide-co-acrylic acid. These polymers may be grafted on to a backbone of chitosan, cellulose, starch, guar gum, carrageenan, alginate, or synthetic polymers such as PVOH.

In some embodiments of the second aspect of the invention, the superabsorbent gel-forming fibre is formed from a polysaccharide. Suitable polysaccharides include alginate (i.e. a salt of alginic acid), modified cellulose, modified chitosan, guar gum, carrageenan, pectin, starch or mixtures thereof. The term 'modified' will be understood as meaning that the polysaccharide molecules have been chemically modified, for example by covalent attachment of additional functional groups. Examples of modified cellulose include carboxymethylcellulose (CMC), cellulose ethyl sulfonate (CES) and cellulose ethyl sulfonate. Examples of modified chitosan include carboxymethylchitosan, ethyl sulfonated chitosan and carboxyethyl chitosan.

In some embodiments of the second aspect of the invention, the superabsorbent gel-forming fibre is not formed from modified cellulose. In some embodiments, the superabsorbent gel-forming fibre is not formed from CES. In some embodiments, the superabsorbent gel-forming fibre is not formed from alginate. In further embodiments, the superabsorbent gel-forming fibre is not formed from a polysaccharide.

In some embodiments, the non gel-forming fibre is a naturally occurring fibre, for example cotton. In other embodiments the non gel-forming fibres are semi-synthetic fibres, in particular semi-synthetic cellulose-based fibres such as rayon (otherwise known as 'viscose' or 'viscose-rayon') or lyocell fibres (formed from solvent spun non-modified cellulose). In other embodiments the non gel-forming fibres are (entirely) synthetic fibres such as nylon fibres (made from polyamides), acrylic fibres (made from polyacetonitriles), or fibres made from polyester or polyolefins (e.g. polypropylene, polyethylene), or co-polymers thereof.

In some particular embodiments, the non gel-forming fibres are lyocell fibres. These may be obtained by an organic solvent spinning process, for example using various amine oxides as solvents. In particular, N-methylmorpholine-N-oxide ("NMNO") with water (about 12%) proves to be a particularly useful solvent. Examples of processes for preparing cellulose fibres are described in McCorsley et al., U.S. Pat. Nos. 4,142,913; 4,144,080; 4,211,574; 4,246,221; and 4,416,698, and others. Jurkovic et al., U.S. Pat. No. 5,252,284 and Michels et al., U.S. Pat. No. 5,417,909 deal especially with the geometry of extrusion nozzles for spinning cellulose dissolved in NMMO. Brandner et al., U.S. Pat. No. 4,426,228 is exemplary of a considerable number of patents that disclose the use of various compounds to act as stabilizers in order to prevent cellulose and/or solvent degradation in the heated NMMO solution. Franks et al., U.S. Pat. Nos. 4,145,532 and 4,196,282, deal with the difficulties of dissolving cellulose in amine oxide solvents and of achieving higher concentrations of cellulose. All of these patents are incorporated herein by reference. Lyocell fibres are commercially available under the brand name 'TEN- CEL'® from Lenzing AG, Austria. Thus, in some embodiments the non gel-forming fibre is TENCEL.

The use of naturally occurring non gel-forming fibres, in particular semi-synthetic fibres such as those based on cellulose, is advantageous because these fibres provide strength while also being capable of absorbing liquid. In some embodiments, the material does not contain any (entirely) synthetic non gel-forming fibres (i.e. the blend of fibres consists of naturally occurring and/or semi-synthetic fibres only). These embodiments are particularly advantageous since there are no non absorbent fibres in the material, thereby maximising the absorbency per gram of material.

In some embodiments, the non gel-forming fibre (in fibre form) is capable of absorbing more than 0.5, more than 0.8, more than 1.0, more than 1.2, more than 1.5 or more than 2.0 g liquid per gram of fibre. In some embodiments, the non gel-forming fibre (in fibre form) is capable of absorbing approximately 1 g of liquid per g of fibre.

In some embodiments, the superabsorbent gel-forming fibre is a polyacrylate (e.g. SAF) and the non gel-forming fibre is a semi-synthetic fibre. In particular embodiments, the superabsorbent gel-forming fibre is polyacrylate (e.g. SAF) and the non gel-forming fibre is a lyocell fibre such as TENCEL.

In some embodiments, the absorbent material comprises at least 30%, at least 40%, at least 50%, at least 60%, at least 70% or at least 80% of the superabsorbent gel-forming fibre, by weight of the total fibre content of the material. In some embodiments, the absorbent material comprises no more than 90%, no more than 80%, no more than 70%, no more than 60%, no more than 50% or no more than 40% of the superabsorbent gel-forming fibre, by weight of the total fibre content of the material.

In some embodiments, the absorbent material comprises at least 10%, at least 20%, at least 30%, at least 40%, at least 50% or at least 60% of the non gel-forming fibre, by weight of the total fibre content of the material. In some embodiments, the absorbent material comprises no more than 70%, no more than 60%, no more than 50%, no more than 40%, no more than 30% or no more than 20% of the superabsorbent gel-forming fibre, by weight of the total fibre content of the material.

In further embodiments, the absorbent material comprises from 30 to 90% or from 40% to 60% of the superabsorbent gel-forming fibre and from 10 to 70% or from 60% to 40% of the non gel-forming fibre, by weight of the total fibre content of the material. In particular embodiments, the material comprises 50% the superabsorbent gel-forming fibre and 50% of the non gel-forming fibre.

In some embodiments, the absorbent material has a weight of no more than 500 g/m², no more than 400 g/m², no more than 300 g/m², no more than 200 g/m², no more than 150 g/m², no more than 120 g/m², no more than 100 g/m², no more than 80 g/m², no more than 60 g/m², no more than 50 g/m² or no more than 40 g/m².

In some embodiments, the absorbent material has an absorbency of more than 18, more than 19, more than 20, more than 22, more than 24, more than 26 or more than 28 grams of liquid (water or saline) per gram of material.

The absorbent material of the invention may be in sheet form. In some embodiments, the material is non-woven. The material may be made by carding, air-laying and/or needle-bonding the fibres, or by or hydro-entangling the fibres using a non-aqueous solvent. In some embodiments, the absorbent material is made by a method comprising carding and, optionally, needle bonding the fibres. Such methods are well-known to those skilled in the art.

The absorbent material may comprise one or more optional ingredients such as preservatives, antimicrobial agents or other pharmacologically active agents. For example, antibiotics (e.g. penicillin), antimicrobial agents (such as silver, PHMB (polyhexamethylene biguanide)), antiseptic agents (e.g. povidone iodine), anti-inflammatory agents (such as hydrocortisone), or other agents (such as zinc oxide) may be included. Such optional agents may be applied to the absorbent material or article by spraying, coating, dipping or by any other method known to those skilled in the art.

According to a third aspect of the present invention there is provided an absorbent article comprising the absorbent material according to the first aspect of the invention.

Absorbent articles may include wound dressings, disposable sanitary articles such as nappies (diapers), disposable nappies and training pants, feminine care products, e.g., tampons, sanitary towels, or napkins and pant liners, and incontinence products. In particular embodiments, the present invention provides a wound dressing comprising the absorbent material in accordance with the first or second aspects of the invention.

In some embodiments, the wound dressing may be in the form of swabs, wound pads, wadding ribbons, sponges, nets and bandages.

The absorbent material of the first aspect of the invention may form one of a plurality of layers. Thus in some embodiments, the wound dressing is a multi-laminar dressing, which may comprise at least 2 or at least 3 layers. Multi-laminar dressings comprising the absorbent material of the invention are more flexible and more absorbent than commercially available multi-laminar dressings, and thus offer improved comfort for the patient. They are also more convenient to use since a single, multi-laminar dressing is simpler and quicker for a care giver to apply to a wound than multiple separate components.

In some embodiments, the wound dressing comprises a first layer comprising or consisting of the absorbent material of the first aspect of the present invention, and a second layer formed from any suitable material. The material of the second layer may be selected according to its desired function. For example, the second layer may provide absorbency, padding, water-proofing or support. A variety of suitable wound dressing materials are commercially available and will be known to those skilled in the art. In some embodiments, the second layer is formed from another, known, absorbent material (such as alginate), which advantageously increases the absorbency of the dressing. In further embodiments, the wound dressing comprises the absorbent material of the first aspect of the present invention bonded to a foam layer. The foam may be a hydrophilic foam such as that described in EP2498829.

In some embodiments, the wound dressing comprises three layers. In some particular embodiments, the wound dressing comprises two outer layers and an inner core, wherein the inner core comprises or consists of the absorbent material of the first aspect of the invention. The outer layers may comprise any suitable material, for example alginate, foam, CES, CMC, or cellulose fluff pulp and a suitable binder. The outer layers may form wound contacting layers. The three-layer combination is useful as a ribbon dressing for cavity wounds. By providing two wound contacting layers and a core layer formed from the absorbent material of the first aspect of the present invention, the absorbency of the dressing is increased compared to existing technology.

In some embodiments, the wound dressing additionally comprises a wound contact layer. The contact layer is the layer which comes into contact with the surface (e.g. of the skin or wound) to which the material is applied. The contact layer conveniently increases the absorbency of the material, and may also help to prevent the material from sticking to the surface. The contact layer may also offer further advantages including providing a moist environment and/or delivering therapeutics or other agents, for example agents conducive to wound healing.

In some embodiments, the wound contact layer is a non-woven or a perforated polymer film, which is applied to one or more surfaces of the dressing. In some embodiments, the wound contact layer comprises or consists of alginate, such as calcium or silver alginate.

In some embodiments, the wound contact layer comprises or consists of alginate, modified cellulosic fibres (such as carboxymethyl cellulose (CMC) or cellulose ethyl sulfonate (CES), hydrogels or foams (e.g. polyurethane, alginate, cellulosic or modified cellulosic foams). Suitable hydrogels may include cross-linked hydrophobic polymers. The polymers may be polysaccharides (e.g. alginates, gelatins, pectins) or synthetic polymers (e.g. polymers based on 2-acrylamido-2-methylpropane sulfonic acid (AMPS), PEG, PVP, PVOH etc.). Suitable hydrogels are commercially available, for example, from Lohmann & Rauscher.

In some embodiments, the wound contact layer comprises or consists of alginate. The alginate salt may comprise a monovalent cation or a multivalent cation, in particular a divalent cation provided that the divalent cation is not $Mg^{2+}$. In some embodiments, the alginate is calcium alginate, sodium calcium alginate, sodium alginate, silver alginate, copper alginate or mixtures thereof. In some embodiments, the alginate is calcium alginate.

Alginate fibres with a range of M/G ratios (the ratio of D-mannuronate to L-guluronate) may be used. A suitable range of M content in the M:G ratio is 30:70 and more preferably 40:60.

The absorbent material of the invention may be attached or bonded to the other materials or layers (such as a wound contact layer) in a multi-laminar wound dressing by any suitable means, such as needle punching, thermal bonding, ultrasonic welding, sewing, stitch bonding, adhesive etc. Such techniques will be well known to those skilled in the art.

Embodiments of the present invention will now be described by way of example only.

EXAMPLES

Example 1

Absorbency

SAF (Technical Absorbents, Grimsby, UK), was carded with TENCEL fibres (Lenzing Fibres, Grimsby, UK) using a sample card and cross folder to produce a carded web. This carded web was needle punched using a TexTex needle loom to give materials A, B and C. Absorbency was measured by weighing a 5 cm×5 cm piece of sample material ($W_1$). Next, the sample was placed in Solution A (16.6 g NaCl and 0.74 g $CaCl_2.2H_2O$ in 2 L water) at 37° C. for 30 minutes in a petri dish. Then, the square was lifted out of the petri-dish by holding the square by one corner, and the sample was allowed to drain for 30 seconds. The sample was then reweighed to obtain the end weight ($W_2$). The fabric absorbency is given by (($W_2-W_1$)/$W_1$).

The retention value of the material was determined for each sample immediately following the absorbency test.

After recording the weight of the sample in the petri dish absorbency test, the sample was placed on blue paper roll (eight layers). A perspex sheet weighing 1358 g and considered to be equivalent to pressure equal to 40 mmHg was placed on top for 30 seconds and then removed. The sample was removed using forceps and weighed. The retention value was determined according to the formula (($W_3-W_1$)/$W_1$) where $W_3$ is the wet weight after compression and $W_1$ is the dry weight.

The absorbency and retention values were measured for the following materials and the results shown in Table 1 below:

A: 40:60 SAF:TENCEL (120 g/m$^2$)

B: 50:50 SAF:TENCEL (120 g/m$^2$)

C: 60:40 SAF:TENCEL (120 g/m$^2$)

D: Calcium alginate

E: DURAFIBER

F: AQUACEL Extra

TABLE 1

| | | A | B | C | D | E | F |
|---|---|---|---|---|---|---|---|
| g/g | Absorbency | 20 | 30 | 23 | 16 | 18 | 12 |
| | Retention | 12 | 17 | 15 | 6 | 11 | 6 |

It can be seen from the data above that at a ratio of 40:60 or 60:40 SAF:Tencel (by weight), both the absorbency and the retention values of the material were improved compared to calcium alginate and other commercial wound dressing products. It was surprisingly observed that at a ratio of 50:50 SAF:Tencel (by weight), both the absorbency and the retention values were significantly increased.

Example 2

Tensile Strength

The tensile strength of materials A-F when wet was measured using the following protocol. The results are shown in Table 2 below.

1. Cut samples in the cross direction (CD)/machine direction (MD) to 10 cm×2.5 cm.
2. Draw a line at 2.5 cm from each end of the sample across the width to give a 5 cm marked section in the middle.
3. Using a Universal Testing Machine (such as those made by Instron), mount the sample so that the edge of each jaw is on the line marked on the fabric
4. Apply 2.5 ml of solution A slowly to the section of fabric between the jaws:
5. Allow to stand for 1 minute.
6. The cross head speed is set to 100 mm/min. Start test and allow the samples to extend to break.
7. Stop test. Remove sample. Return cross head to start position.
8. The software calculates the breaking load, extension and tensile strength in N/cm.

TABLE 2

| Wet Tensile strength (N/cm) | A | B | C | E | F | G |
|---|---|---|---|---|---|---|
| MD | 11.3 | 8.0 | 7.0 | 1.0 | 2.5 | 2.4 |
| CD | 18.7 | 19.5 | 8.8 | 1.9 | 3.8 | 7.2 |

It can be seen from the data in Table 2 that the wet tensile strength of the SAF: TENCEL blends (materials A, B and C) was significantly increased in both the machine direction and the cross direction compared to the known materials. The wet tensile strength of the 50:50 SAF:TENCEL blend was more than 3-fold greater in the machine direction, and more than 2.5-fold greater in the cross direction, than that of the commercial wound dressings (F and G). Surprisingly, the wet tensile strength of the 40:60 SAF:TENCEL blend in the machine direction was more than 4-fold greater than that of the commercial products and more than 10-fold greater than that of the calcium alginate.

The invention claimed is:

1. An absorbent material comprising a blend of a superabsorbent gel-forming fibre and a non gel-forming fibre, wherein the blend of fibres does not comprise a superabsorbent gel-forming fibre formed from a polysaccharide, wherein the non gel-forming fibre is a semi-synthetic fibre, and wherein the absorbent material consists of 50% of the superabsorbent gel-forming fibre and 50% of the non gel-forming fibre by weight of the total fibre content of the material; and
   wherein the superabsorbent gel-forming fibre is formed from a cross-linked polymer of acrylic acid (AA), methylacrylate (MA) and special acrylate/methylacrylate monomer (SAMM) and wherein the non gel-forming fibre is lyocell fibre.

2. An absorbent material according to claim 1, wherein the material has an absorbency of more than 18 grams of liquid per gram of material.

3. A wound dressing comprising the absorbent material according to claim 1.

4. The absorbent material according to claim 1, wherein the material is in the form of a non-woven sheet.

5. The absorbent material according to claim 4, wherein the material is formed by needle-bonding the fibres.

6. The wound dressing according to claim 3, wherein the wound dressing comprises a wound contact layer comprising or consisting of a polysaccharide.

* * * * *